(12) United States Patent  (10) Patent No.: US 9,033,535 B2
Robinson  (45) Date of Patent: May 19, 2015

(54) LIGHTING CONTROL SYSTEM FOR UTILITY HELMET

(71) Applicant: Levi Jacob Robinson, Somis, CA (US)

(72) Inventor: Levi Jacob Robinson, Somis, CA (US)

(73) Assignee: Levi Jacob Robinson, Balcom Canyon Road ( * ) Notice: Subject to any disclaimer, the term of this patent is extended or adjusted under 35 U.S.C. 154(b) by 0 days.

(21) Appl. No.: 14/179,834

(22) Filed: Feb. 13, 2014

(65) Prior Publication Data

US 2014/0376210 A1 Dec. 25, 2014

Related U.S. Application Data

(62) Division of application No. 12/925,832, filed on Oct. 30, 2010, now Pat. No. 8,721,103.

(51) Int. Cl.
| | |
|---|---|
| A61F 9/06 | (2006.01) |
| F21V 21/36 | (2006.01) |
| F21V 23/04 | (2006.01) |
| F21V 33/00 | (2006.01) |
| F21K 99/00 | (2010.01) |
| F21W 131/402 | (2006.01) |
| F21Y 113/00 | (2006.01) |

(52) U.S. Cl.
CPC ............ *F21V 23/0492* (2013.01); *F21V 33/008* (2013.01); *F21V 23/0414* (2013.01); *F21V 23/04* (2013.01); *F21K 9/58* (2013.01); *F21W 2131/402* (2013.01); *F21Y 2113/005* (2013.01)

(58) Field of Classification Search
CPC ....... A61F 9/061; A61F 9/064; A42B 3/0433; A42B 3/044
USPC .......................... 362/105, 106, 271, 276; 2/8.2
See application file for complete search history.

(56) References Cited

U.S. PATENT DOCUMENTS

| | | | | |
|---|---|---|---|---|
| 4,958,264 | A * | 9/1990 | Evendon | 362/106 |
| 6,070,264 | A * | 6/2000 | Hamilton et al. | 2/8.8 |
| 7,934,846 | B1 * | 5/2011 | Schwanz | 362/106 |
| 8,025,432 | B2 * | 9/2011 | Wainright | 362/394 |
| 8,497,465 | B2 * | 7/2013 | Hammond | 250/221 |
| 2007/0089216 | A1 * | 4/2007 | Walkden | 2/8.7 |

* cited by examiner

*Primary Examiner* — Karabi Guharay

(57) ABSTRACT

A control system for automatically switching power between two separate light sources integrated with a welding shield pivotally mounted to an adjustable headband includes at least one magnetic positional switch attached to the headband having electrical communication with at least one battery and the light sources, and two magnetic positional sensors strategically mounted on the interior surface of the welding shield along a defined arcurate path of rotation of the shield about the headband.

8 Claims, 8 Drawing Sheets

LIGHTING CONTROL SYSTEM FOR UTILITY HELMET

CROSS-REFERENCE TO RELATED DOCUMENTS

The present invention is a Divisional application from U.S. application Ser. No. 12/925,832, filed Oct. 30, 2010, and claims priority to a U.S. provisional patent application Ser. No. 61/280,382 entitled SAFETY HELMET WITH LIGHTING SYSTEM filed on Nov. 3, 2009 disclosure of which is incorporated herein in its entirety at least by reference.

BACKGROUND OF THE INVENTION

1. Field of the Invention

The present invention is in the field of safety gear including workplace utility helmets and pertains particularly to methods and apparatus for adapting a welding helmet, also referred to as a welding shield with a controlled lighting system that may be operated in automated fashion.

2. Discussion of the State of the Art

In many industries like manufacturing and construction, welding is a common practice. Welders wear welding helmets, sometimes referred to as welding shields or face shields, during the course of their work. Generally speaking, a welding shield is constructed to pivot about the workers head and typically has two positions. One position is with the shield down during actual welding to protect the workers eyes and face from extreme light from the welding arc and from any debris that could be dislodged during the process. Periodically, the worker must raise the shield so the worker can see the workspace for weld preparation, cleaning, and other tasks performed during the course of welding.

One challenge with welding using so-called welding helmets or shields, is that many workspaces where welding occurs are not sufficiently illuminated. Therefore, extra work must be undertaken to set-up lighting for these areas. The shield lens of a welding shield is typically colored or darkened like sunglasses in order to protect a worker's eye from extreme light flashing that occurs during the process of active arc welding. These lenses are to dark for the user to see the workspace without the light from active welding contributing to errors in the process resulting in poor quality. Self-darkening lenses for welding shields are available that darken only when extreme light is present. However, insufficient lighting still contributes to workspace errors during welding when the shield is lowered and when the shield is raised.

Therefore, what is clearly needed is a protective welding helmet or shield integrated with a lighting system that may be controlled to illuminate the workspace in a focused manner using the welding shield. A shield such as this would eliminate the problems stated above.

SUMMARY OF THE INVENTION

A control system is provided for automatically switching power between two separate light sources integrated with a welding shield pivotally mounted to an adjustable headband. The control system includes at least one magnetic positional switch attached to the headband having electrical communication with at least one battery and the light sources, and two magnetic positional sensors strategically mounted on the interior surface of the welding shield along a defined arcurate path of rotation of the shield about the headband.

One of the two magnetic positional sensors is aligned with the magnetic positional switch at the lowermost rotational position of the welding shield relative to the headband, the alignment causing current to flow to one of the two light sources and wherein at the uppermost rotational position of the shield relative to the headband the other of the two magnetic positional sensors is aligned over the magnetic positional switch causing is current to flow to the other of the two light sources.

In one embodiment, both light sources are powered off when no magnet is in alignment over the magnetic positional switch. In another embodiment, one of the light sources remains powered on as long as the other light source is powered off. In one embodiment the control system further includes a manual switch that can override the positional switch.

In one embodiment one or both light sources are LEDs of differing colors. In this embodiment the color combination may include a bright white light and a softer yellow light. In one embodiment one or both light sources have an adjustable focus capability to emit a more focused and narrow beam or a wider and less focused beam according to need. In one embodiment one or both light sources are directionally adjustable.

BRIEF DESCRIPTION OF THE DRAWING FIGURES

DETAILED DESCRIPTION

The inventor provides a unique welding shield with integrated lighting and lighting control system. The present invention will be described in enabling detail using the following examples, which may describe more than one relevant embodiment falling within the spirit and scope of the present invention.

Figure 1:
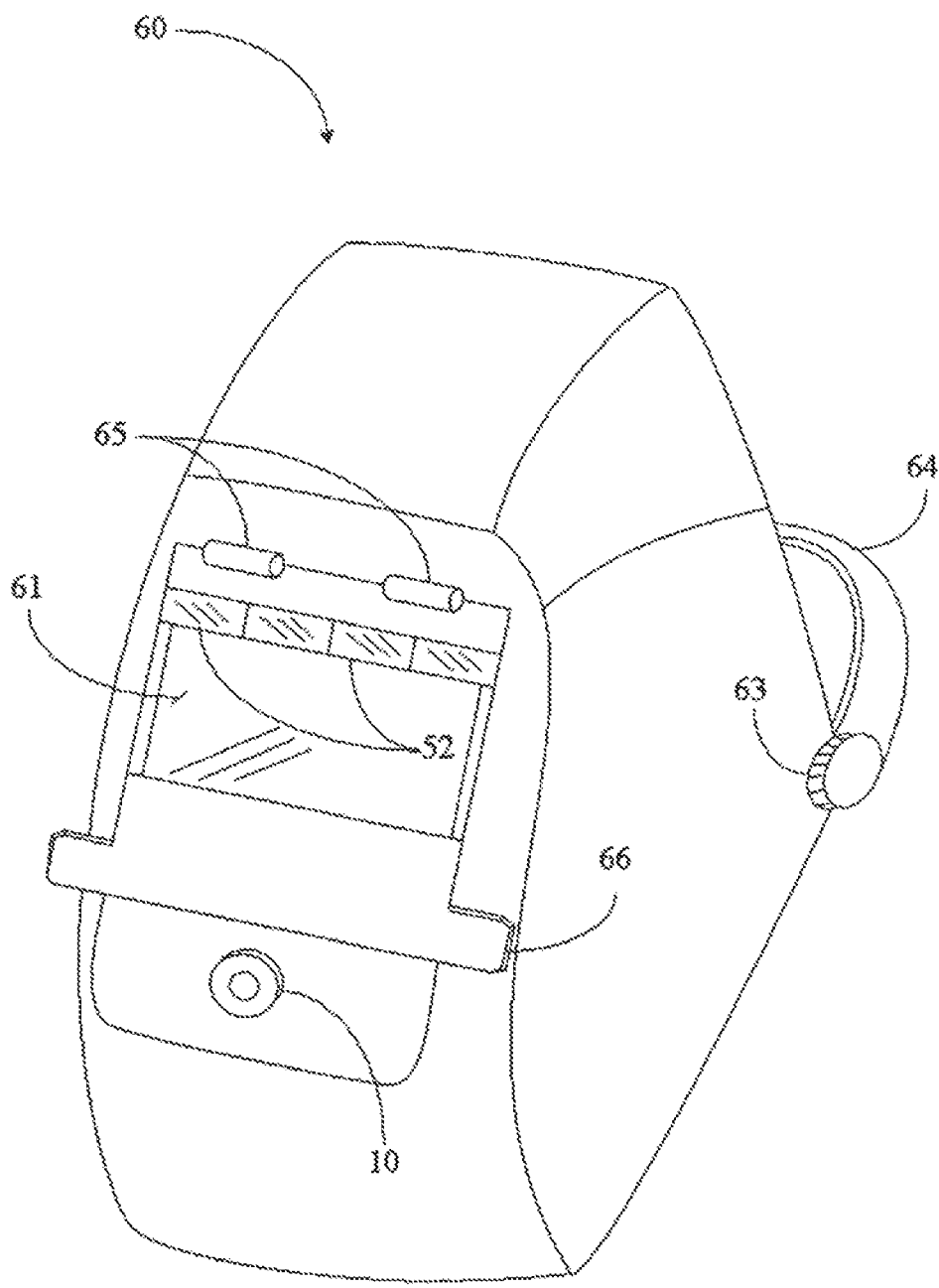
FIG. 1 is a perspective view of a welding shield 60 according to an embodiment of the present invention.

FIG. 1 is a perspective view of a welding shield 60 according to an embodiment of the present invention. Welding shield 60 may also be referred to herein as a face shield or helmet-face shield without departing from the spirit and scope of the present invention. The term welding shield is a well-known industry term for a welding helmet.

In this example, shield 60 includes a welding shield lens 61 attached to shield 60 by way of one or more hinges 65. Shield lens 61 may be an auto-darkening lens, a shaded lens, or a transparent protective viewing lens without departing from the spirit and scope of the present invention. Shield lens 61 is in the closed position. Lens 61 includes user operable tabs 66 to facilitate easy opening of the lens.

Welding shield 60 is pivotally mounted to an adjustable headband 64 by frictional locking knobs 63. A user places the headband over the head and adjusts the position of welding shield 60, typically raising or lowering the shield using locking knobs 63 to lock the adjusted opposition. In one embodiment of the present invention, shield lens 61 may include solar cells 52 mounted thereon and adapted to enable charging of the lighting system of the welding shield.

Welding shield 60 includes a light emitter 10. Light emitter or light source 10 may be alight emitting diode (LED) 10 mounted on the front area of welding shield 60. Light source 10 may be physically integrated into the surface wall of welding shield 60 or it may be treaded thereon, snapped thereon, glued thereon or affixed thereon using some other attachment method. Light source 10 may be adjustable in one embodiment to output a stronger more focused light beam or a wider less focused light beam. Welding shield 60 may be molded of a durable polymer material or composite material. Hinges 65 may be frictionally controlled to help secure welding shield lens 61 in an upright position. Light emitter 10 may be encapsulated in a high strength plastic, composite material, or other materials. Light source 10 is mounted on the outer face of welding shield 60 in an area that enables optimum illumination of a desired workspace area.

Figure 2:
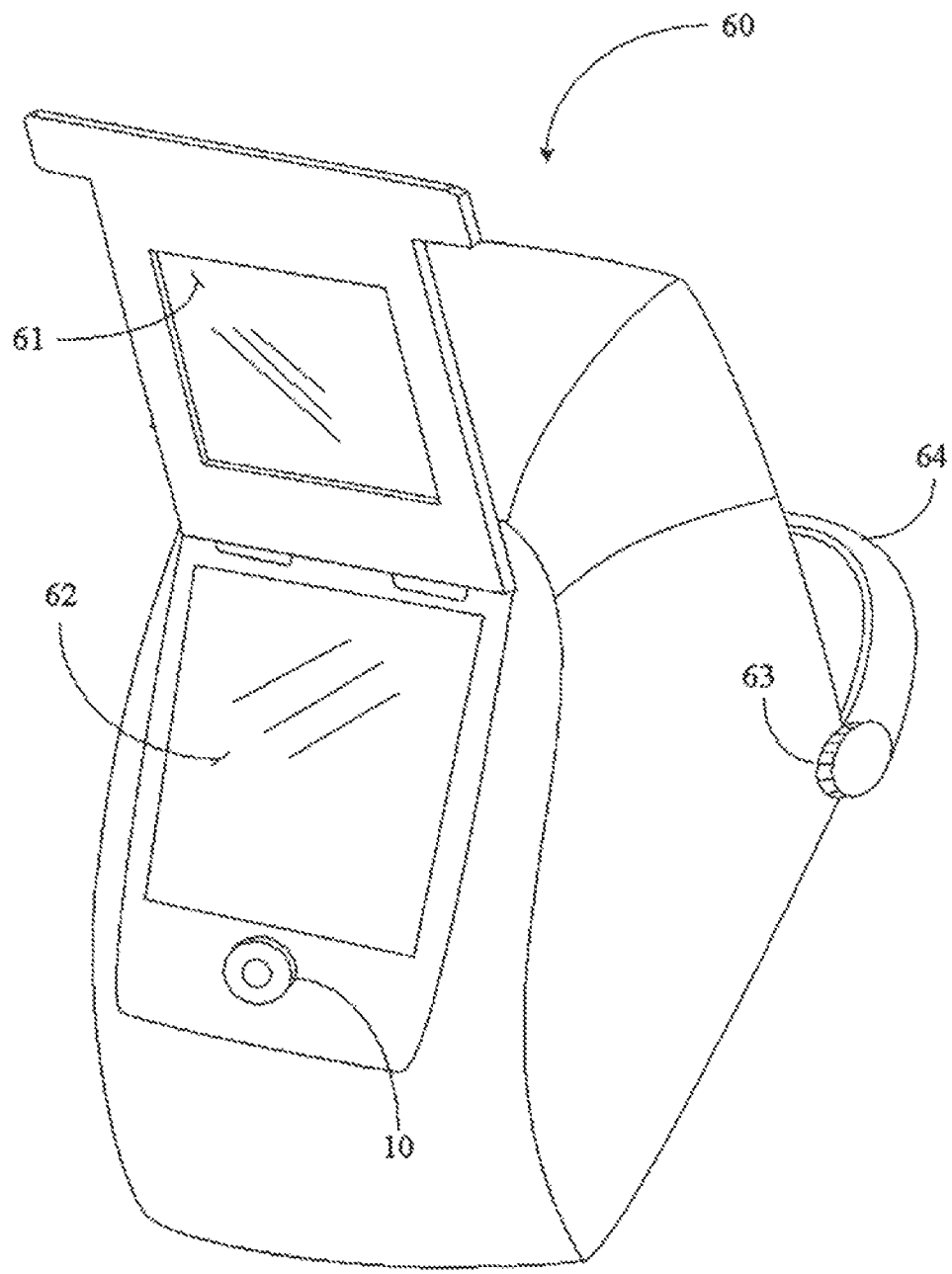
FIG. 2 is a perspective view of the shield of FIG. 1 with a shield lens open revealing a second transparent lens.

FIG. 2 is a perspective view of welding shield 60 of FIG. 1 shield lens 61 open revealing a second transparent lens. Welding shield 60 includes a second transparent viewing lens 62 that provides protective viewing option with the darker lens removed or raised. Lenses 61 and 62 may be manufactured of a resilient and shatter-resistant polymer material suitable for safety lens manufacture. In one embodiment tens 62 is removable from welding shield 60. With welding shield 60 in the lowered position, light emitter 10 may be powered on automatically to provide illumination for the operator viewing the area through the darkened lens or through the secondary transparent lens 62.

Figure 3:
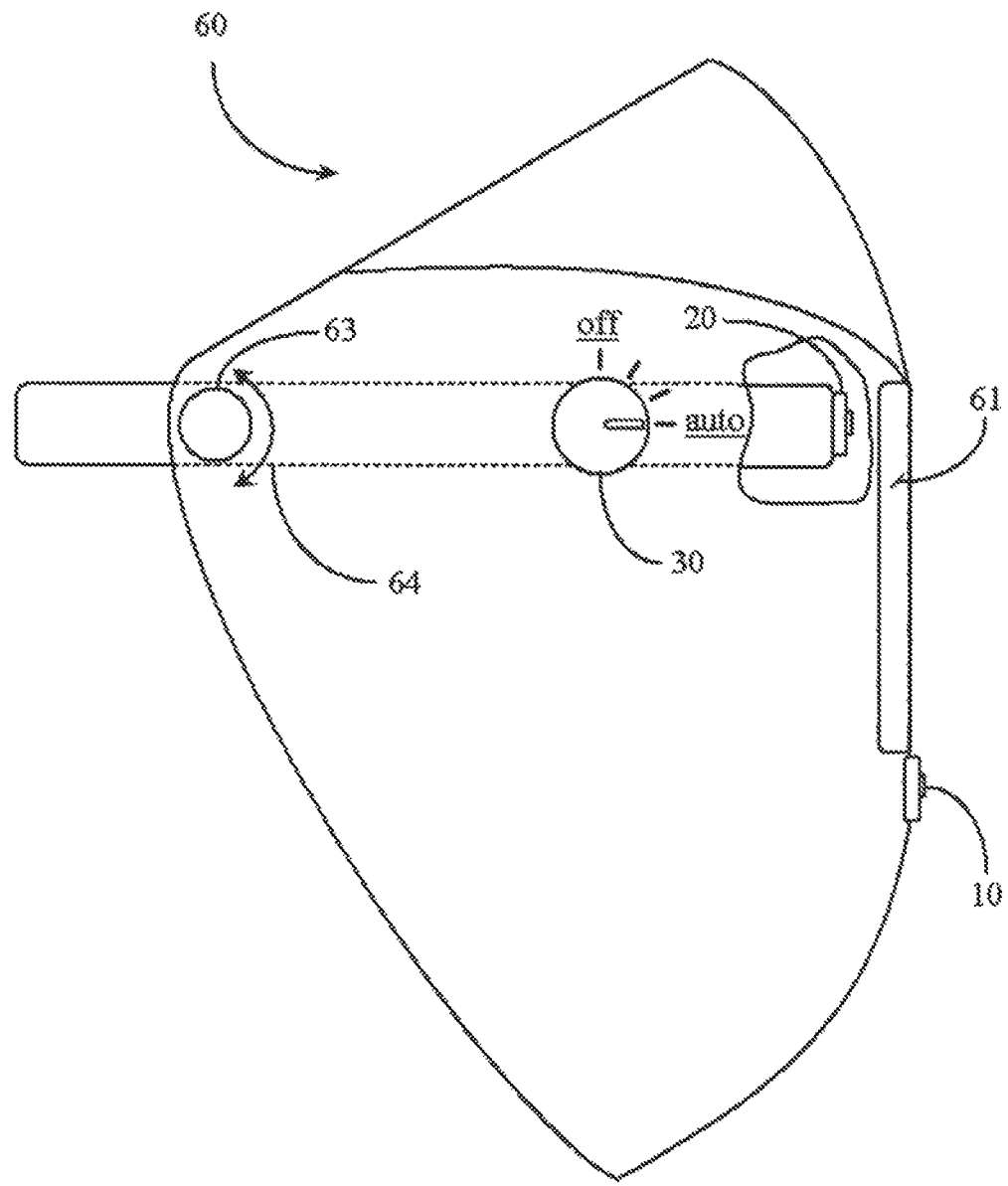
FIG. 3 is a side view of the shield of FIG. 1 illustrating a manual lighting system control switch with an of and an auto setting.

FIG. 3 is a side view of welding shield 60 of FIG. 1 illustrating a manual lighting system control switch with an off setting and an auto setting. Welding shield 60 has an integrated lighting system of which light source 10 is part of as described further above. Headband 64 has a headband light source 20 fixed thereto. Light source 20 may be an LED in one embodiment. In one embodiment, light source 20 has a focusing capability and can be adjusted to throw a more focused and narrow beam or a wider and less focused beam according to need. In one embodiment light sources 10 and 20 are directionally adjustable to a degree.

Welding shield 60 may be raised or lowered about pivot positions created by frictional locking knobs 63 (one illustrated). Headband 64 provides an electrical communication pathway for laying the wire needed for integrating the two lighting control system available for the welding shield. Headband 64 may be manufactured from a durable but flexible polymer composite or material. A portion of welding shield 60 is removed in this example to permit view of lighting source 20.

Welding shield 60 includes a manual control dial 30 adapted for controlling the integrated lighting system of both the welding shield and the headband. In this example, dial 30 is a rotational dial having at least four settings that are selectable by an operator. One setting is off, selection thereof causing both lighting source 20 and lighting source 10 to be powered off. A next setting may be a setting, which causes power to be delivered to the welding shield external lighting source 10.

Welding shield 60 is lowered into a position for welding and darkened shield lens 61 is closed. In this position it is desirable that lighting source 10 is powered on. A third setting may cause power to be delivered to the headband lighting source 20. Lighting source 20 would be powered on when welding shield 60 is raised to an elevated position thus exposing the headband lighting source to the workspace area. The fourth setting for rotary dial 30 is automatic or auto. Automatic or auto causes diversion from manual lighting control to automatic lighting control. Auto mode is operated in a preferred embodiment by raising and lowering the welding shield about its pivot points or frictional knobs 63. More detail about operating auto mode to alternately illuminate the described lighting sources will be provided later in this specification.

Figure 4:
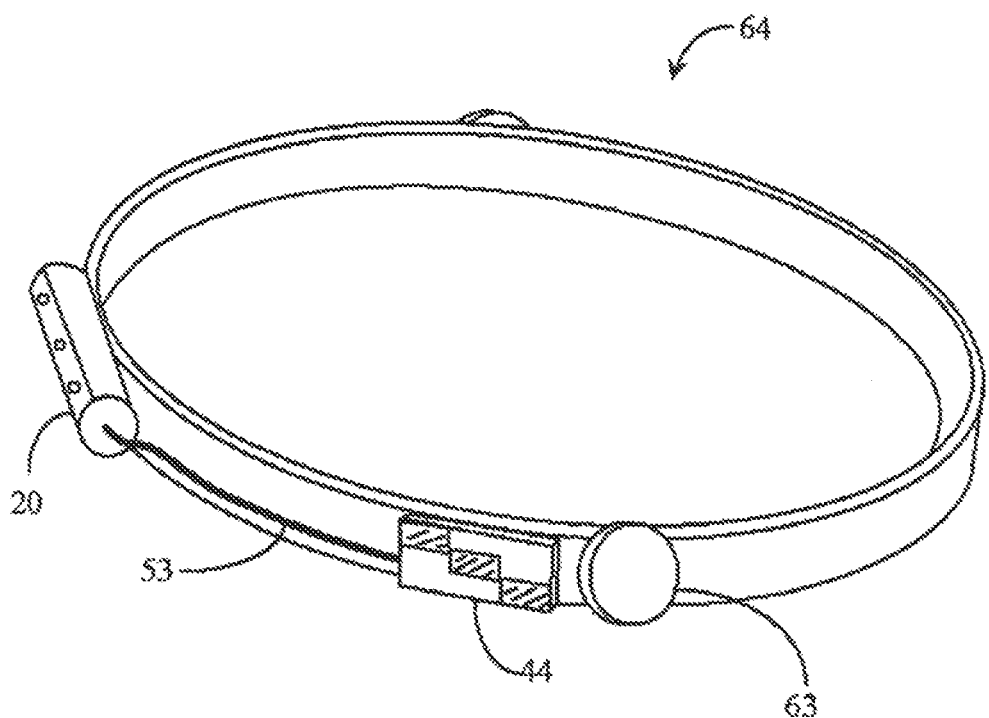
FIG. 4 is a perspective view of a headband lighting system leveraging a magnetic reed switch for powering on a mounted light source according to an embodiment of the present invention.

FIG. 4 is a perspective view of a headband lighting system leveraging a magnetic reed switch 44 for powering on a mounted light source according to an embodiment of the present invention. Switch 44 may comprise a magnetically operated switch for powering on headband lighting source 20 illustrated on the front portion of headband 64. Locking knobs 63 are illustrated in this example. Lighting source 20 may be adjustable in direction, focus, and power without departing from the spirit and scope of the present invention. Light source 20 communicates with switch 44 via an electrical wiring 53. In this example, a positional magnet on the inside of welding shield 60 passes over switch 44 when the welding shield is raised sufficiently causing the headband light 20 to power on.

Figure 5:
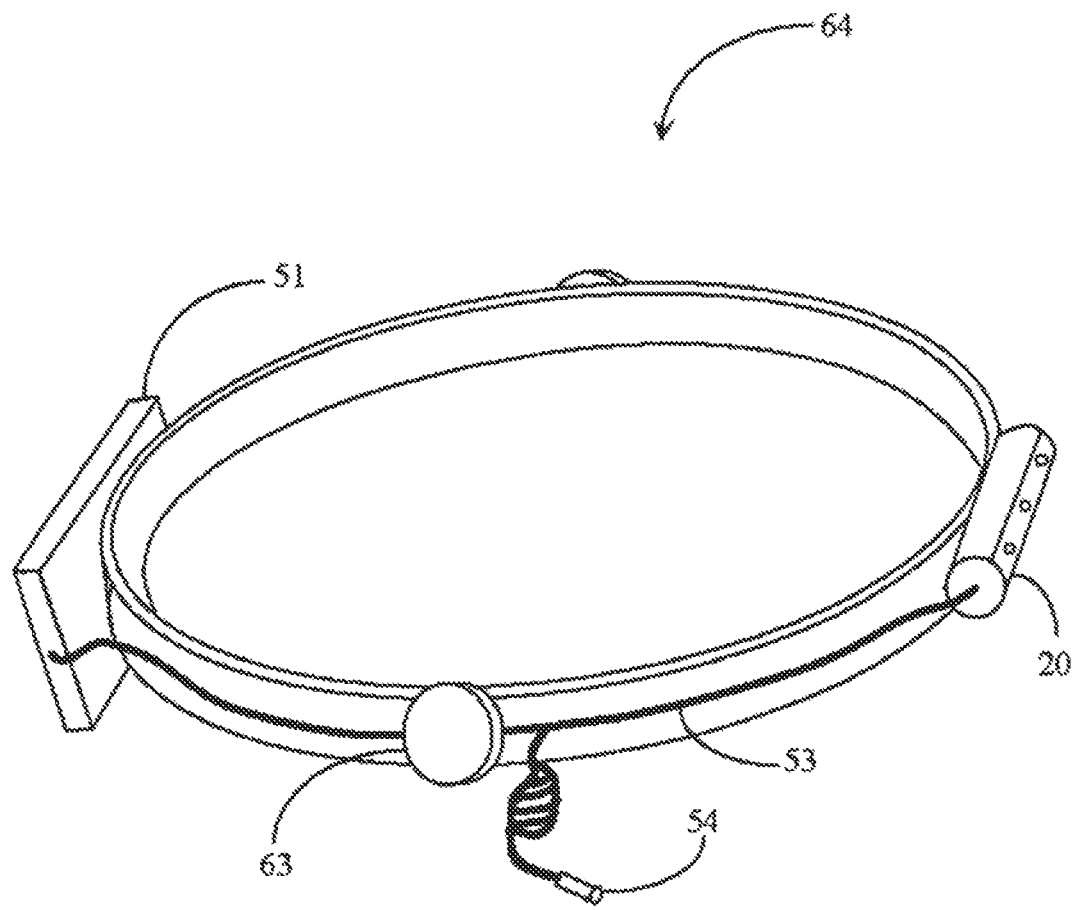
FIG. 5 is a perspective view of a headband lighting system leveraging a battery and having a connector to a shield lighting system.

FIG. 5 is a perspective view of a headband lighting system leveraging a battery and having a connector to a shield lighting system. Headband 64 supports headband lighting source 20. Lighting source 20 is connected to a battery 51 by wiring 53. Battery 51 may be a rechargeable battery that can be charged electronically or by solar power. There may be more than one battery for supplying power to the integrated lighting system of the welding shield without departing from the spirit and scope of the present invention.

In this example, wiring 53 includes an extendable plug 54 for connecting to the portion of the lighting system that is used to power on light emitter 10 described previously in this specification. Wiring 53 may be standard power electrical wiring of a gage suitable for illuminating emitters 10 and 20. In one embodiment, lighting source 20 fixed to headband 64 includes LEDs of differing colors like bright white light and yellow "soft" light.

Figure 6:
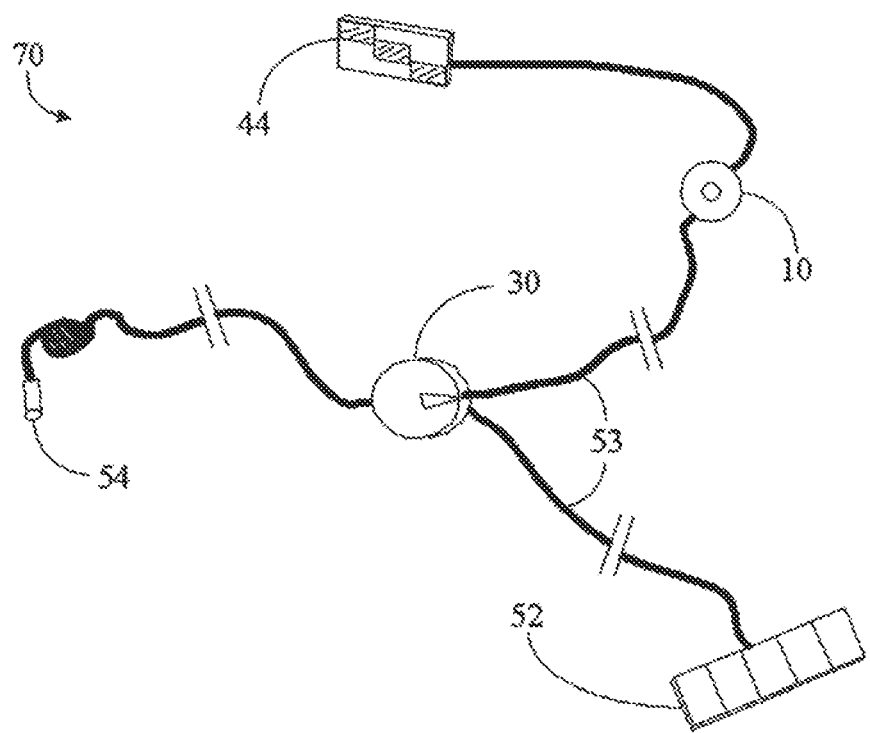
FIG. 6 is a cable lighting system for retrofitting to a welding shield according to an embodiment of the present invention.

FIG. 6 is a cable lighting system 70 for retrofit to a welding shield according to an embodiment of the present invention. In one embodiment of the present invention a stock-welding shield is retrofitted with a cable lighting system 70. Lighting system 70 includes a connector plug 54 analogous to the connector plug of FIG. 5 above. Wiring 53 includes wiring from plug 54 to a mountable manual control dial 30, analogous to control dial 30 of FIG. 3 above. Wiring 53 continues on one path to welding shield light emitter 10 and positional sensor switch 44 for automatic operation. Wiring 53 continues from dial 30 on another path to solar cell array 52. The components of FIG. 6 are adapted to be retrofit to a stock welding helmet or shield.

Figure 7:
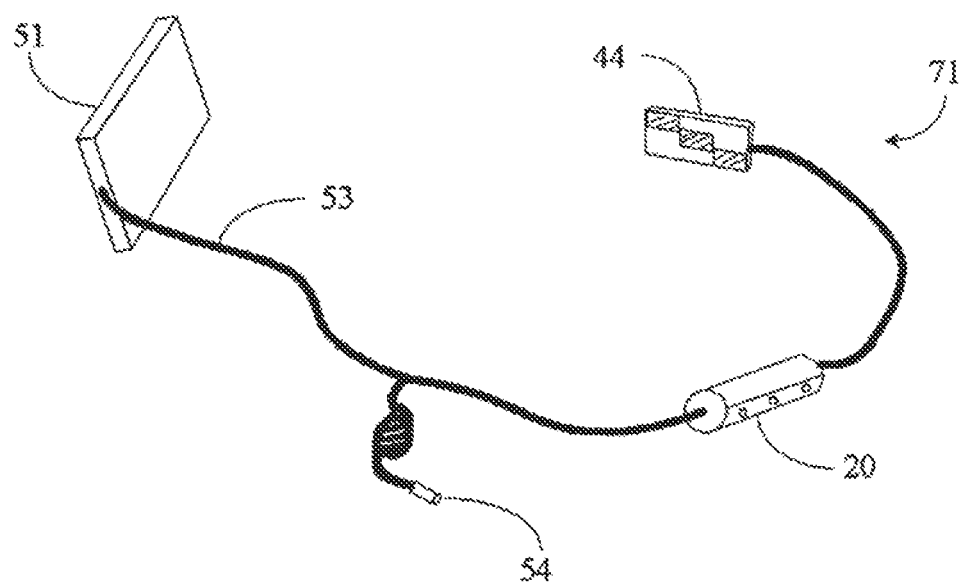
FIG. 7 is a cable lighting system for retrofitting to a welding shield headband according to an embodiment of the present invention.

FIG. 7 is a cable lighting system 71 for retrofit to a welding shield headband according to an embodiment of the present invention. Light emitter 20 has connection via wiring 53 to positional sensor 44, which would mount to a headband of a welding shield. At the other end of light emitter 20 is battery 51. Plug 54 enables connection to the other system 70. The components of FIG. 7 are adapted to retrofit to a stock welding shield headband.

Figure 8:
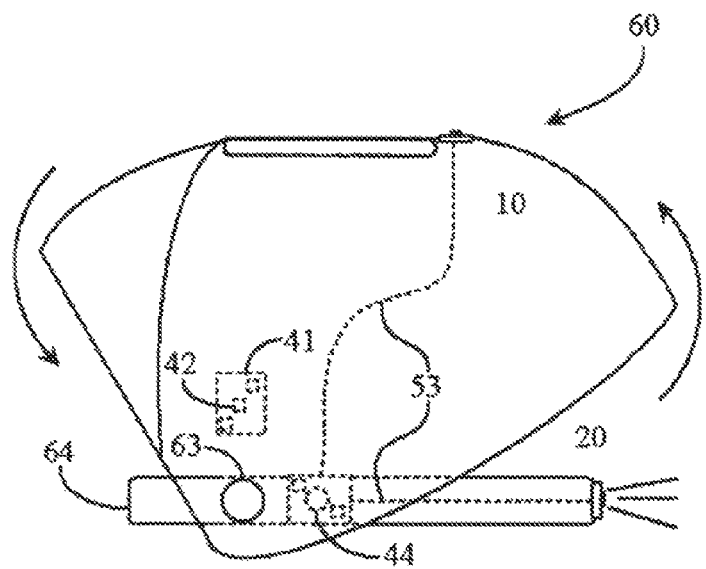
FIG. 8 is a side view of the welding shield of FIG. 1 adapted with a positional switching system, the shield raised to power on the headband light source.

FIG. 8 is a side view of welding shield 60 of FIG. 1 adapted with a positional switching system, the shield raised to power on the headband light source. Welding shield 60 is illustrated in a raised position relative to headband 64 exposing headband light source 20 to illuminate the workspace. A positional switch or magnetic reed switch 44 fixed to headband 64 is in alignment beneath one of magnets 42 mounted on positional sensor 41 that is mounted to the interior surface of the welding shield. Positional sensor 41 is mounted strategically in the arcurate path of rotation of the shield relative to the positional switch 44 mounted on the headband.

In this example, wiring 53 includes a path leading from switch 44 to headband light source 20 that is activated by switch 44 to power on lighting source 20 when shield 60 is raised as illustrated in this example by the direction of the rotational arrows. A second positional sensor 41 hosting earth or electromagnets 42 is illustrated in broken boundary indicating a mounted position on the interior surface of shield 60. The second positional sensor 41 aligns with positional switch 44 when welding shield 60 is lowered.

Figure 9:
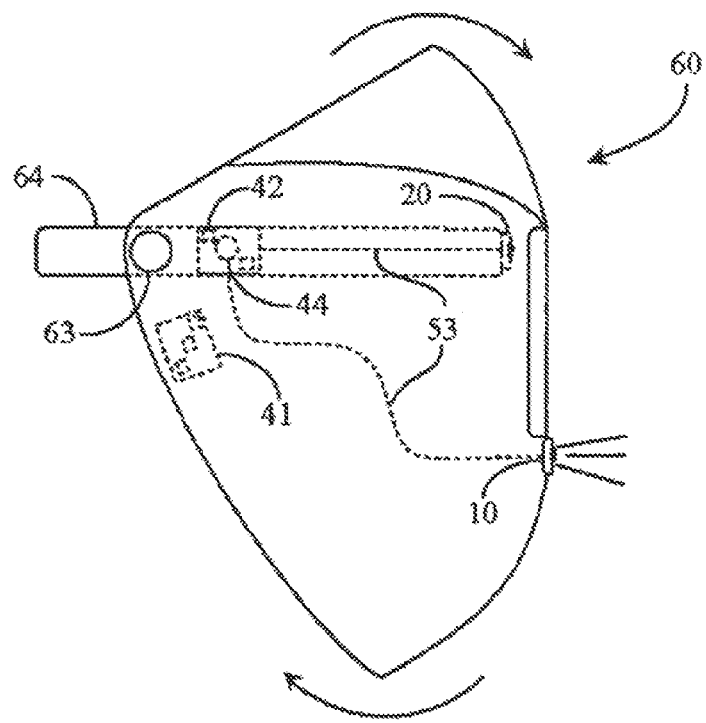
FIG. 9 is a side view of the welding shield of FIG. 1 adapted with a positional switching system, the shield lowered to power on the welding shield light source.

FIG. 9 is a side view of welding shield 60 of FIG. 1 adapted with a positional switching system, the shield lowered to power on the welding shield tight source. Welding shield 60 is illustrated in a lowered position relative to headband 64 exposing headband light source 10 to illuminate the workspace. Positional switch 44 fixed to headband 64 is in alignment beneath one of magnets 42 mounted on a positional sensor 41, which in turn is mounted to the interior surface of shield 60. As described above, positional sensor 41 is mounted strategically in the &curate path of rotation of the shield relative to the positional switch 44 mounted on the headband.

In this example, wiring 53 includes a path leading from switch 44 to welding shield tight source 10 that is activated by switch 44 to power on lighting source 10 when shield 60 is lowered as illustrated in this example by the direction of the rotational arrows. The first-described positional sensor 41 and electromagnets or earth magnets 42 is illustrated as fixed to the interior surface of the welding shield in a arcurate rotational path relative to switch 44 on the headband and comes into alignment with switch 44 when the shield is again raised.

Figure 10:
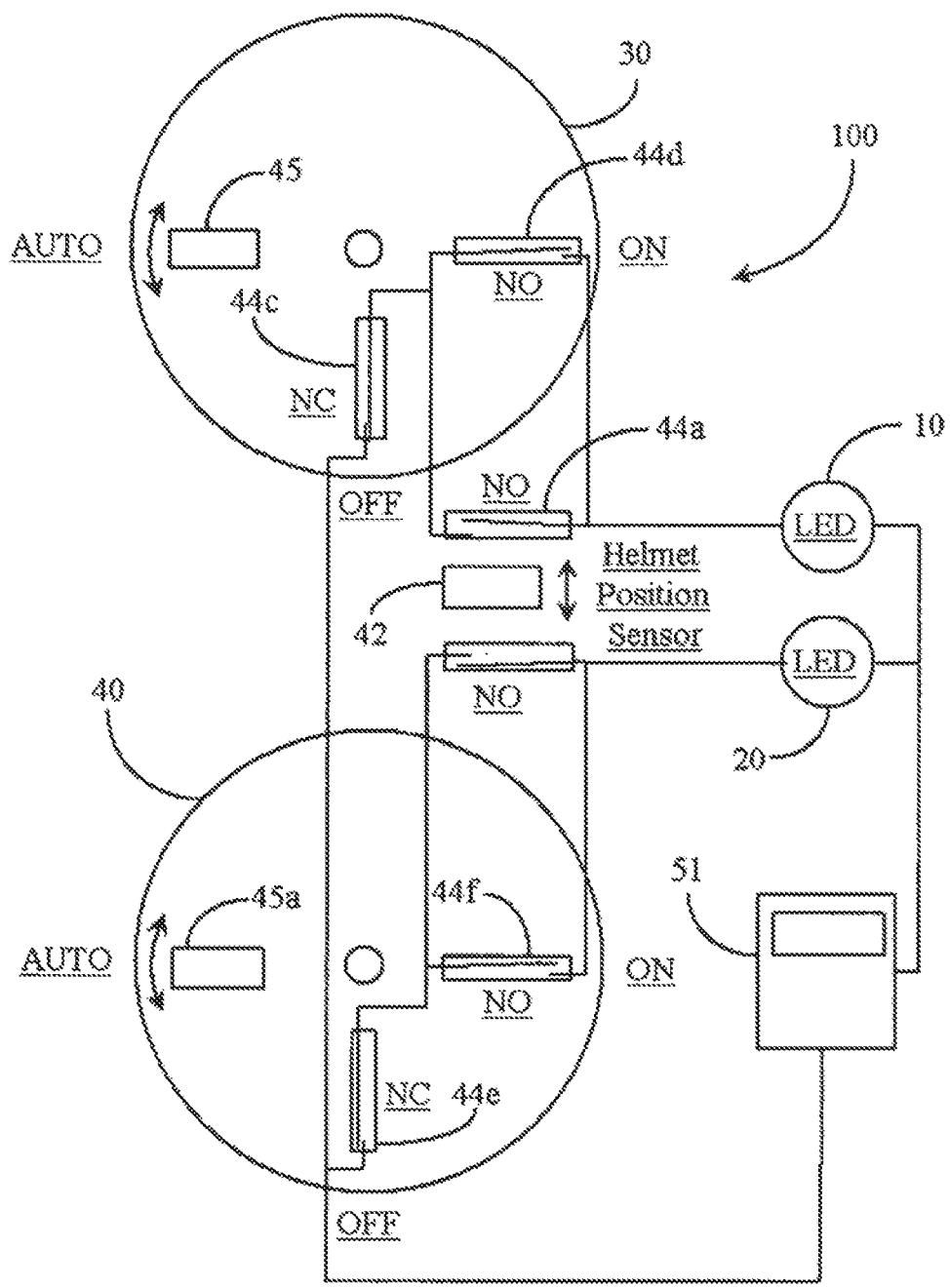
FIG. 10 is a circuitry diagram illustrating a manual lighting control circuit with an automatic positional sensing switch setting.

FIG. 10 is a circuitry diagram illustrating a manual lighting control circuit 100 with an automatic positional sensing switch setting. Control circuit 100 represents one embodiment of the present invention. Dial 30 controls the flow of electricity from battery 51 in this example to welding shield light emitter 10. In this case light emitter 10 is an LED but in another embodiment another illumination device may be used instead.

Alternate control unit or dial 40 may be provided to control the flow of electricity from battery 51 to headband light emitter 20. A magnet 45 is mounted on dial 30 and is moved in a rotational path as the dial is physically turned as illustrated by rotational arrow. Dial 40 includes a similar magnet 45a.

When magnets 45 and 45a are both in the auto position as shown, normally closed (NC) magnetic reed switch 44c is closed and normally open (NO) magnetic reed switches 44d and 44a are open, therefore no current flows from battery 51 to light emitter 10 causing light emitter 10 to be off. If however, helmet 60 is placed in a lowered position, electro magnet 42 is brought close to magnetic reed switch 44a causing closure of the switch resulting in current flowing from battery 51 to light emitter 10 illuminating the workspace.

Similarly, when both magnets 45 and 45a are in the auto position as shown NC magnetic reed switch 44e is closed and NO magnetic reed switches 44f and 44b are open, therefore no current flows from battery 51 to light emitter 20 causing light emitter 20 to be off. However, if the welding shield is raised to the uppermost position, magnet 42 is brought close to magnetic reed switch 44b causing current to flow from battery 51 to light emitter 20 resulting in illumination of the workspace.

When control dial 40 is turned is physically turned so that magnet 45a is in the ON position, magnetic reed switch 44f is closed enabling flow of current from battery 51 to light emitter 20 resulting in illuminating the workspace regardless of whether magnetic reed switch 44b is open or closed overriding that circuit causing light emitter 20 to remain on regardless of raising or lowering the helmet. Likewise, when control dial 4 is turned such that the magnet 45a is in the off position, magnetic reed switch 44e opens blocking current flow from battery 51 to light emitter 20 causing light emitter 20 to remain off regardless of whether magnetic reed switch 44b is in the open or closed position. Therefore, light emitter 20 remains off in the manual mode regardless of whether the welding shield is raised or lowered.

In general use of the welding shield lighting system of the present invention, an operator may don the welding shield adjusting the headband for good fit. In manual mode a user may select from manual settings OFF, Welding Shield Light ON Headband Light ON, or AUTO. Selecting AUTO cause the system to defer to automatic mode wherein alternate light emitters are powered on based on welding shield position.

The "automatic" setting uses a positional sensor to control the light emitters. The user may select the desired light emitter by positioning the welding shield in relation to the headband. If the welding shield is in the lowered position, then the helmet light emitter 10 is powered on. If the welding shield is in the raised position, then the headband tight emitter 20 is powered on. Each light emitter turns off when the alternate light emitter is activated.

In the solar cell-enabled charging system, the battery power supply is charged through the use solar of cells 52, converting energy from the ultraviolet light emission of the welding activity or sunlight into electrical power. Electrical power is communicated by way of power cable/wire 53 and electrical connectors or plugs 54 Supplemental, charging may be allowed for by plugging into an external power source between uses.

It will be apparent to one with skill in the art that the welding shield and lighting control system of the invention may be provided using some or all of the mentioned features and components without departing from the spirit and scope of the present invention. It will also be apparent to the skilled artisan that the embodiments described above are specific examples of a single broader invention, which may have greater scope than any of the singular descriptions taught. There may be many alterations made in the descriptions without departing from the spirit and scope of the present invention.

What is claimed is:

1. A control system for automatically switching power between two separate light sources integrated with a welding shield pivotally mounted to an adjustable headband comprising:
- at least one magnetic positional switch attached to the headband having electrical communication with at least one battery and the light sources; and
- two magnetic positional sensors strategically mounted on the interior surface of the welding shield along a defined arcurate path of rotation of the shield about the headband;
- wherein at the lowermost rotational position of the welding shield relative to the headband, one of the two magnetic positional sensors is aligned with the magnetic positional switch causing current to flow to one of the two light sources and wherein at the uppermost rotational position of the shield relative to the headband the other of the two magnetic positional sensors is aligned over the magnetic positional switch causing current to flow to the other of the two light sources.

2. The control system of claim 1, wherein both light sources are powered off when no magnet is in alignment over the magnetic positional switch.

3. The control system of claim 1, wherein one of the light sources remains powered on as long as the other light source is powered off.

4. The control system of claim 1, further including a manual switch that can override the positional switch.

5. The control system of claim 1 wherein one or both light sources are LEDs of differing colors.

6. The control system of claim 5 wherein the differing colors are a bright white light and a softer yellow light.

7. The control system of claim 1 wherein one or both light sources have an adjustable focus capability to emit a more focused and narrow beam or a wider and less focused beam according to need.

8. The control system of claim 1 wherein one or both light sources are directionally adjustable.

* * * * *